United States Patent
Lee et al.

(10) Patent No.: US 8,044,245 B2
(45) Date of Patent: Oct. 25, 2011

(54) METHOD FOR THE PREPARATION OF OPTICALLY ACTIVE 2-SULFONYLOXY-1-PHENYLETHANOL DERIVATIVES

(75) Inventors: Kee-In Lee, Daejeon (KR); Do-Min Lee, Gunsan-si (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 279 days.

(21) Appl. No.: 12/513,097

(22) PCT Filed: Nov. 1, 2007

(86) PCT No.: PCT/KR2007/005492
§ 371 (c)(1),
(2), (4) Date: Apr. 30, 2009

(87) PCT Pub. No.: WO2008/054155
PCT Pub. Date: May 8, 2008

(65) Prior Publication Data
US 2010/0063317 A1     Mar. 11, 2010

(30) Foreign Application Priority Data

Nov. 1, 2006   (KR) ........................ 10-2006-0107059

(51) Int. Cl.
C07C 315/00   (2006.01)
B01J 31/00    (2006.01)
C07F 15/00    (2006.01)

(52) U.S. Cl. ............................ 568/28; 568/814; 502/155
(58) Field of Classification Search ................. 568/814, 568/28; 502/155
See application file for complete search history.

(56) References Cited

OTHER PUBLICATIONS

Peach, P., et al., "Asymmetric transfer hydrogenation of α,β-unsaturated, α-tosyloxy and α-substituted ketones," Tetrahedron, 62, 2006, 1864-1876.
Cross, D.J., et al., "Rhodium versus ruthenium: contrasting behaviour in the asymmetric transfer hydrogenation of α-substituted acetophenones," Tetrahedron: Asymmetry 12 (2001) 1801-1806.
Cho, B.T., et al., "Convenient synthesis of optically active 1,2-diol monosulfonates and terminal epoxides via oxazaborolidine-catalyzed asymmetric borane reduction of α-sulfonyloxy ketones," J. Chem. Soc., Perkin Trans. 1, 2001, 1204-1211.
Kim, D.J., et al., "A New Approach to the Synthesis of Optically Active Norephedrine, Norpseudoephedrine and Cathinone via Double Asymmetric Induction," Bull. Korean Chem. Soc., 24:11, 2003. pp. 1641-1648.

*Primary Examiner* — Porfirio Nazario Gonzalez
(74) *Attorney, Agent, or Firm* — Sughrue Mion, PLLC

(57) ABSTRACT

Optically active 2-sulfonyloxy-1-phenylethanol derivative of formula (II) can be prepared easily and selectively by the method of the present invention using an asymmetric reduction of an α-sulfonyloxy acetophenone compound with a rhodium catalyst having petamethylcyclopentadienyl group and a hydrogen donor, and the compound of formula (II) obtained in the inventive method exhibits a higher e.e. (enantiomer excess) value than that of the products in the conventional methods.

3 Claims, No Drawings

METHOD FOR THE PREPARATION OF OPTICALLY ACTIVE 2-SULFONYLOXY-1-PHENYLETHANOL DERIVATIVES

FIELD OF THE INVENTION

The present invention relates to an efficient method for preparing highly optically active 2-sulfonyloxy-1-phenylethanol derivatives.

BACKGROUND OF THE INVENTION

Optically active 2-amino-1-phenylethanol derivatives of formula (I) have been used in the preparations of several agricultural chemicals, medical supplies, fine chemicals and building blocks, and 60 biologically active substances having 2-amino-1-phenylethanol moiety have been identified to date.

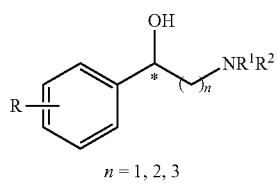

(I)

$n = 1, 2, 3$

Representative examples of drugs containing 2-amino-1-phenylethanol derivatives include blockbuster drugs such as Paroxetine (Paxil, anti-depression agent) and Salmeterol (Seretide, anti-asthma agent) (*Chemistry Today* (2006), 24, 40); currently available drugs such as Fluoxetin (Prozac), Sotalol (Betapace), Formotero (Foradil) and Fexofenadine (Allegra), which are derived from chiral switches in the pipeline (*Nature Rev. Drug Discov.* (2002), 1, 753-768); adrenoceptor agonists such as Tulobuterol, Metaproterenol, Fenoterol and Terbutaline; and NR1/2B subtype NMDA receptor antagonists such as Ifenprofil and Eliprodil. Further, there are several candidate drugs having 2-amino-1-phenylethanol moiety under development, which include adrenoceptor agonists such as Albuterol, Calcimimetics, Terbutaline, Ritodrine, Salmeterol, Suloctidil and Synephrine; NR1/2B subtype NMDA receptor antagonists such as CP-101,606 and Ro-25-6981 (*Bioorg. Med. Chem. Lett.* (2002), 12, 2615-2619); antidiabetics (U.S. Pat. No. 5,817,689); anti-obesity agents (U.S. Pat. No. 5,817,689 and *J. Med. Chem.* (1999), 42, 181-201); and anti-depressants (U.S. Pat. No. 4,707,497 and *Tetrahedron* (2001), 57, 1849-1855).

Generally, the compound of formula (I) is prepared by a conventional method using essential intermediates of formulae (II) to (IV).

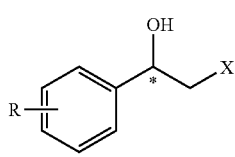

(II)

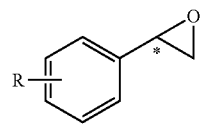

(III)

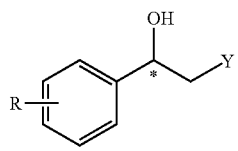

(IV)

wherein, X is a halogen atom such as —Cl and —Br, or a leaving group such as mesyloxy (—OMs) and tosyloxy (—OTs); Y is —NH$_2$, primary or secondary amine, —N$_3$, or —CN; and R is hydrogen, halogen, alkyl, hydroxy, amine, —NO$_2$ or —CF$_3$ substituted in the ortho-, metha- or para-position of the phenyl group.

Accordingly, there have been numerous attempts to develop the preparations of optically active intermediates of formulae (II) to (IV). For example, a number of studies disclosed the methods for preparing the compound of formula (II) or (IV), comprising asymmetric reduction of α-substituted acetophenones using oxazaborolidine catalyst and borane (*Angew. Chem. Int. Ed.* (1998), 37, 1986-2012; *Tetrahedron Lett.* (1997), 38, 1125-1128; and *Tetrahedron Lett.* (2001), 42, 8919-8921), asymmetric reduction of α-substituted acetophenones using asymmetric transfer hydrogenation (*Org. Lett.* (2005), 7, 5489-5491; *Org. Lett.* (2002), 4, 4373-4376; and Japanese Patent Publication No. 2002-251994); asymmetric reduction of aminoketone using hydrogen at high pressure (*J. Am. Chem. Soc.* (2000), 122, 6510-6511); synthesis of diol using asymmetric dihydroxylation (*Tetraderon: Asymmetry* (2004), 15, 3955-3959); asymmetric acylation of α-azidoalcohol using enzymes (*Tetraderon: Asymmetry* (2004), 15, 3939-3944); or reduction of α-azidoketone using microorganisms (*Tetraderon: Asymmetry* (2001), 12, 3381-3385; and *J. Mol. Cat. B: Enzymatic* (2006), 39, 9-12).

Among these methods, the asymmetric reduction of α-substituted acetophenones using oxazaborolidine catalyst and borane is mainly employed in the preparation of the compound of formulae (II) to (IV); however, such method require high cost due to the use of an expensive catalyst in an excess amount, and have the wide fluctuation of the optical activity of the product depending on the substitution of the phenyl moiety, in addition, the reduction is highly sensitive to humidity.

Further, the asymmetric reduction of aminoketone using hydrogen at high pressure can be conducted only when the amino group of aminoketone is disubstituted, it is difficult to derivatize the product thereof, and the hydrogen gas used in the reduction is danger.

Although the asymmetric reduction of α-substituted acetophenones using asymmetric transfer hydrogenation is an effective method for the preparation of the intermediates, α-substituent of acetophenones such as —Cl, —N$_3$ or —CN is known to be harmful to the skin and eyes. Furthermore, it is difficult to apply the method on the mass production due to its poor light stability, and low e.e. (enantiomer excess) value of the product thereof, e.g., α-azido- or α-cyano-acetophenone.

SUMMARY OF THE INVENTION

Accordingly, it is an object of the present invention to provide an efficient method for preparing optically active 2-sulfonyloxy-1-phenylethanol derivatives. In accordance with one aspect of the present invention, there is provided a method for preparing an optically active 2-sulfonyloxy-1-phenylethanol derivative of formula (II), comprising i) reacting (pentamethylcyclopentadienyl)rhodium(III) chloride dimer ([Rh($C_5Me_5$)$Cl_2$]$_2$) with optically active 1,2-diphenylethylene-N-(p-toluenesulfonyl)diamine (TsDPEN) in methylene chloride and optionally in the presence of triethylamine, and removing the solvent from the reaction product to obtain a rhodium compound; and ii) conducting asymmetrical reduction of an α-sulfonyloxy acetophenone compound in the presence of the rhodium compound having pentamethylcyclopentadienyl group as a catalyst and a hydrogen donor:

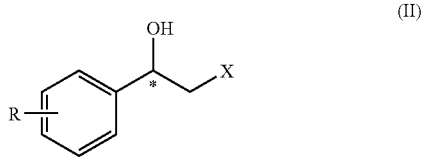

(II)

wherein,

X is tosyloxy or mesyloxy;

R is one or more substituents, each independently, selected from the group consisting of H, F, Cl, Br, OH, OMe, OBn, OAc, OTBS, OTs, $NH_2$, NHBn, NHBz, NHTBS, NHMs, $N(Ac)_2$, $N(Ms)_2$, $NO_2$, $CF_3$, Me, tert-Bu and $CH_2OMe$ substituted in the ortho-, metha- or para-position of the phenyl moiety, the substituents being optionally fused together to form a benzene, dioxane or dioxolane ring (Me=methyl, Bn=benzyl, Bu=butyl, Bz=benzoyl, TBS=tert-butyldimethylsilyl, Ms=mesyl, Ac=acetyl, and Ts=tosyl).

DETAILED DESCRIPTION OF THE INVENTION

In the present invention, the compound of formula (II) can be prepared in a high e.e. value by asymmetrically reducing α-sulfonyloxy acetophenone compound in the presence of a rhodium compound of formula (V) or (VI) as a catalyst.

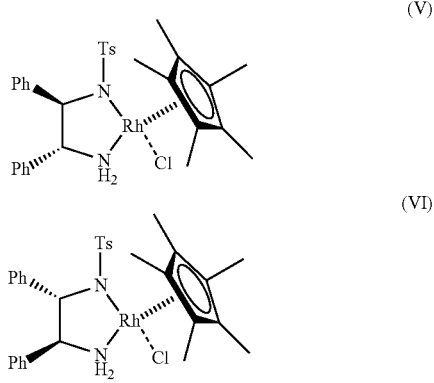

The rhodium catalyst of formula (V) used in the inventive method is a known material referred to as "TsDPEN-RhCl-Cp*" in the art.

Particularly, the rhodium catalyst has been disclosed in several papers, e.g., Mashima et al., *Chem. Letters* (1998), 1199-1200 and *Chem. Letters* (1998), 1201-1202, which demonstrates that the rhodium catalyst can be obtained in a yield of 70% by reacting 1 equivalent of (pentamethylcyclopentadienyl)rhodium(III) chloride dimer ([Rh($C_5Me_5$)$Cl_2$]$_2$), 2 equivalent of optically active 1,2-diphenylethylene-N-(p-toluenesulfonyl)diamine (TsDPEN) and 4 equivalent of triethylamine in methylene chloride, and washing and recrystallizing the reaction mixture.

In the method of the present invention, the rhodium catalyst of formula (V) may be prepared by methods (A) and (B) described below, and the compound of formula (VI) may be also employed as a catalyst instead of the compound of formula (V):

Method (A)—reacting 1 equivalent of (pentamethylcyclopentadienyl)rhodium(III) chloride dimer ([Rh($C_5Me_5$)$Cl_2$]$_2$), 2 equivalent of optically active 1,2-diphenylethylene-N-(p-toluenesulfonyl)diamine (TsDPEN) and 4 equivalent of triethylamine in methylene chloride as a solvent to obtain a reaction mixture, and removing the solvent from the reaction mixture to obtain the catalyst of formula (V) in a quantitative yield; and Method (B)—reacting 1 equivalent of (petamethylcyclopentadienyl)rhodium(III) chloride dimer ([Rh($C_5Me_5$)$Cl_2$]$_2$) and 2 equivalent of optically active 1,2-diphenylethylene-N-(p-toluenesulfonyl)diamine (TsDPEN) in methylene chloride as a solvent, in the absence of triethylamine, to obtain a reaction mixture, and removing the solvent from the reaction mixture to obtain the catalyst of formula (V) in a stoichiometric yield.

The compound of formula (V) can be easily and efficiently prepared by the methods (A) and (B) in a higher yield than that of the conventional methods, and therefore, the compound of formula (II) obtained in the asymmetrical reduction of α-chloro acetophenones using the catalyst of formula (V) or (VI) exhibits a higher e.e. (enantiomer excess) value than that of the products obtained in the conventional methods.

The asymmetrical reduction according to the inventive method is summarized in Reaction Scheme I.

Reaction Scheme I

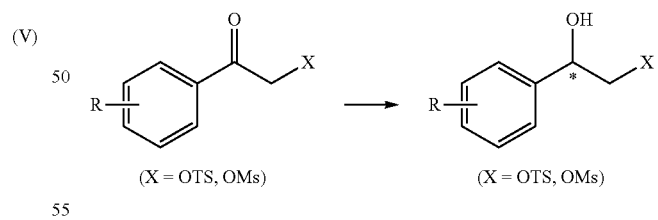

(X = OTS, OMs)    (X = OTS, OMs)

The α-sulfonyloxy acetophenone compound used in the above process may be prepared by a conventional method; for instance, the α-tosyloxy acetophenone compound may be prepared by reacting acetophenone with [hydroxy(tosyloxy)iodido]benzene (which is also referred to as "Koser's reagent") in accordance with a method described in [*J. Org. Chem.* (1982), 47, 2487-2489], and similarly, the α-mesyloxy acetophenone compound may be prepared by reacting acetophenone with [hydroxyl(mesyloxy)iodido]benzene, as shown in Reaction Scheme II.

Reaction Scheme II

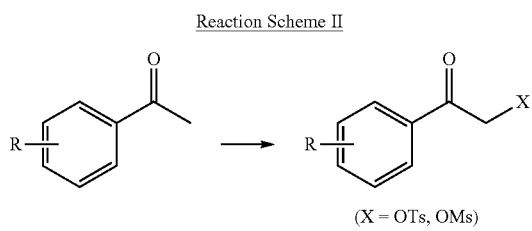

(X = OTs, OMs)

In the inventive method, it is preferred that a hydrogen donor, which is a compound capable of providing hydrogen by the action of heat or catalysis, is employed, and the exemplary hydrogen donor includes formic acid, a metal or ammonium salt thereof, or an azeotropic mixture of formic acid and an amine such as triethylamine.

In case of employing formic acid, a salt thereof, or an azeotropic mixture of formic acid and an amine as a hydrogen donor, the asymmetric reduction of the inventive method may be carried out in the presence of an optional solvent, the solvent may be selected from the group consisting of ethylacetate, toluene, methylene chloride, dimethylformamide (DMF), dimethylsulfoxide (DMSO), tetrahydrofuran (THF), acetonitrile and isopropanol.

The α-sulfonyloxy acetophenone compound used as a starting material in the inventive method may be employed in an amount ranging from 100 to 100,000 moles, preferably 1,000 to 10,000 moles based on the metal in the catalyst.

The method of the present invention may further comprise conventional purification steps such as extraction, distillation, recrystallization and column chromatography for the purpose of increasing the purity of the product.

The following Examples are intended to further illustrate the present invention without limiting its scope.

The e.e. values of the 1-phenylethane-1,2-diol monosulfonate compounds obtained in the following Examples were determined by HPLC using a column equipped with Chiralcel OD-H, DB-H and OJ-H (Diacel).

Preparation Example 1

Preparation of [S,S]-TsDPEN-RhCl-Cp*/Et$_3$N.HCl 0.10 g (0.16 mmol) of dichloro(pentamethylcyclopentadienyl)rhodium(III) dimer and 0.12 g (0.32 mmol) of (1S,2S)-(−)-N-p-tosyl 1,2-diphenylethylenediamine were placed in a 25 ml two-necked round flask under an argon atmosphere, 5 ml of anhydrous methylene chloride and 90 μl (0.65 mmol) of anhydrous triethyleneamine were added thereto, and the mixture was stirred at room temperature for 2 hrs. The reaction mixture was concentrated under a reduced pressure to remove the solvent and dried for 2 hrs under a high vacuum to obtain 190 mg of the title compound as an orange-colored powder. The obtained compound was kept under an argon atmosphere during the experimental periods of the following Examples.

Preparation Example 2

Preparation of [R,R]-TsDPEN-RhCl-Cp*/Et$_3$N.HCl 12.5 mg (0.02 mmol) of dichloro(pentamethylcyclopentadienyl)rhodium(III) dimer and 14.6 mg (0.04 mmol) of (1R,2R)-(−)-N-p-tosyl-1,2-diphenylethylenediamine were placed in a 25 ml two-necked round flask under an argon atmosphere, 2 ml of anhydrous methylene chloride and 11.5 μl (0.08 mmol) of anhydrous triethyleneamine were added thereto, and the mixture was stirred at room temperature for 2 hrs. The reaction mixture was concentrated under a reduced pressure to remove the solvent and dried for 2 hrs under a high vacuum to obtain 35 mg of the title compound as an orange-colored powder. The obtained compound was kept under an argon atmosphere during the experimental periods of the following Examples.

Preparation Example 3

Preparation of [R,R]-TsDPEN-RhCl-Cp*

6.3 mg (0.01 mmol) of dichloro(pentamethylcyclopentadienyl)rhodium(III) dimer and 7.3 mg (0.02 mmol) of (1R,2R)-(−)-N-p-tosyl-1,2-diphenylethylenediamine were placed in a 25 ml two-necked round flask under an argon atmosphere, 1 ml of anhydrous methylene chloride was added thereto, and the mixture was stirred at room temperature for 2 hrs. The reaction mixture was concentrated under a reduced pressure to remove the solvent and dried for 4 hrs under a high vacuum to obtain 12 mg of the title compound as an orange-colored powder. The obtained compound was kept under an argon atmosphere during the experimental periods of the following Examples.

Preparation Example 4

Preparation of [S,S]-TsDPEN-RhCl-Cp*

12.3 mg (0.02 mmol) of dichloro(pentamethylcyclopentadienyl)rhodium(III) dimer and 14.6 mg (0.04 mmol) of (1S,2S)-(−)-N-p-tosyl-1,2-diphenylethylenediamine were placed in a 25 ml two-necked round flask under an argon atmosphere, 1 ml of anhydrous methylene chloride was added thereto, and the mixture was stirred at room temperature for 2 hrs. The reaction mixture was concentrated under a reduced pressure to remove the solvent and dried for 4 hrs under a high vacuum to obtain 12 mg of the title compound as an orange-colored powder. The obtained compound was kept under an argon atmosphere during the experimental periods of the following Examples.

Example 1

Preparation of (R)-(−)-1-phenyl-2-(p-tolylsulfonyloxy)ethanol 290 mg (1 mmol) of 1-phenyl-2-(p-tolylsulfonyloxy)ethanone and 0.8 mg (0.001 mmol) of [S,S]-TsDPEN-RhCl-Cp*/Et$_3$N.HCl obtained in Preparation Example 1 were placed in a 10 ml round flask, and the flask was sealed. After introducing argon gas therein for 10 mins, 2.5 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 4 hrs and subjected to a column chromatography to obtain the title compound (yield: 97%).

$[\alpha]_D^{25} = -51.3$ (c=2.54, CHCl$_3$), chiral HPLC: 95.0% e.e. (Chiralcel OD-H, 250×4.6 mm, hexane:ethanol=95:5, 0.5 ml/min), $^1$H NMR. (300 MHz, CDCl$_3$) δ 7.78 (2H, d, J=8.4 Hz); 7.36-7.27 (7H, m); 4.99 (1H, d, J=8.7 Hz); 4.17 (1H, dd, J=10.2 and 3.3 Hz); 4.07 (1H, dd, J=10.2 and 8.7 Hz); 2.55 (OH, d, J=3 Hz); 2.44 (3H, s).

Example 2

Preparation of (R)-(−)-1-(2-methoxyphenyl)-2-(p-tolylsulfonyloxy)ethanol 320 mg (1 mmol) of 1-(2-methoxyphenyl)-2-(p-tolylsulfonyloxy)ethanone and 0.8 mg (0.001 mmol) of [S,S]-TsD-PEN-RhCl-Cp*/Et$_3$N.HCl obtained in Preparation Example 1 were placed in a 10 ml round flask, and the flask was sealed. After introducing argon gas therein for 10 mins, 2.5 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 4 hrs and subjected to a column chromatography to obtain the title compound (yield: 99%).

$[\alpha]_D^{25}=-47.9$ (c=2.54, CHCl$_3$), chiral HPLC: 84.6% e.e., $^1$H NMR (300 MHz, CDCl$_3$) δ 7.76 (d, 2H, J=8.1), 7.38-7.24 (m, 4H), 6.95 (t, 1H, J=7.5), 6.82 (d, 1H, J=8.1), 5.17 (dd, 1H, J=3.3, 8.1), 4.30-4.00 (m, 2H), 3.77 (s, 3H), 2.44 (s, 3H).

Example 3

Preparation of (R)-(−)-1-(3-methoxyphenyl)-2-(p-tolylsulfonyloxy)ethanol 320 mg (1 mmol) of 1-(3-methoxyphenyl)-2-(p-tolylsulfonyloxy)ethanone and 0.8 mg (0.001 mmol) of [S,S]-TsD-PEN-RhCl-Cp*/Et$_3$N.HCl obtained in Preparation Example 1 were placed in a 10 ml round flask, and the flask was sealed. After introducing argon gas was introduced therein for 10 mins, 2.5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 96%).

$[\alpha]_D^{25}=-37.5$ (c=2.56, CHCl$_3$), chiral HPLC: 93.7% e.e., $^1$H NMR (300 MHz, CDCl$_3$) δ 7.77 (d, 2H, J=8.4), 7.33 (d, 2H, J=8.1), 7.27-7.22 (m, 1H), 6.88-6.82 (m, 3H), 4.98-4.93 (m, 1H), 4.17-4.00 (m, 2H), 3.79 (s, 3H), 2.45 (s, 3H).

Example 4

Preparation of (R)-(−)-1-(4-methoxyphenyl)-2-(p-tolylsulfonyloxy)ethanol 1.602 g (5 mmol) of 1-(4-methoxyphenyl)-2-(p-tolylsulfonyloxy)ethanone and 3.89 mg (0.005 mmol) of [S,S]-TsD-PEN-RhCl-Cp*/Et$_3$N.HCl obtained in Preparation Example 1 were placed in a 100 ml round flask, and the flask was sealed. After introducing argon gas therein for 10 mins, 35 ml of ethylacetate was added thereto to completely dissolve the starting materials, and 1 ml of a mixture of formic acid and triethylamine (5:2, molar ratio) were added thereto. When the color of the reaction mixture changed from light yellow to dark red after 2 to 3 mins, the reaction mixture was stirred at room temperature for 18 hrs and subjected to a column chromatography to obtain the title compound (yield: 92%).

$[\alpha]_D^{25}=-49.5$ (c=2.51, CHCl$_3$), 93.6% e.e., $^1$H NMR (300 MHz, CDCl$_3$) δ 7.77 (d, 2H, J=8.4), 7.33 (d, 2H, J=8.1), 7.23 (d, 2H, J=7.2), 6.86 (d, 2H, J=8.7), 4.92 (dd, 1H, J=3.5, 8.4), 4.13-4.00 (m, 2H), 3.79 (s, 3H), 2.45 (s, 3H).

Example 5

Preparation of (R)-1-(4-benzyloxyphenyl)-2-(p-tolylsulfonyloxy)ethanol 4.36 g (11 mmol) of 1-(4-benzyloxyphenyl)-2-(p-tolylsulfonyloxy)ethanone and 9 mg (0.011 mmol) of [S,S]-TsD-PEN-RhCl-Cp*/Et$_3$N.HCl obtained in Preparation Example 1 were placed in a 100 ml round flask, and the flask was sealed. After introducing argon gas therein for 10 mins, 22 ml of ethylacetate was added thereto to completely dissolve the starting materials, and 2.2 ml of a mixture of formic acid and triethyamine (5:2, molar ratio) was added thereto. The resulting mixture was stirred at room temperature for 6 hrs and washed with water, and the combined organic layer was dried over anhydrous sodiumsulfate and filtered. The obtained residue was subjected to a column chromatography to obtain the title compound (yield: 82%).

mp 91-92° C., $^1$H NMR (300 MHz; CDCl$_3$) δ 7.77 (2H, d, J=8.4 Hz), 7.43-7.32 (6H, m), 7.26-7.20 (3H, m), 6.93 (2H, d, J=8.8 Hz), 5.05 (2H, s), 4.95 (1H, dt, J=8.3 and 3.0 Hz), 4.13-3.99 (2H, m), 2.44 (3H, s), $^{13}$C NMR. (DMSO-d$_6$) δ 158.90, 145.04, 136.71, 132.62, 130.51, 129.91, 128.59, 128.02, 127.93, 127.49, 127.40, 114.98, 74.28, 71.49, 69.98, 21.65;

EIMS (70 eV) m/z (relative intensity) 398 (M$^+$, 1), 213 (56), 91 (100);

$[\alpha]_D^{28}-42.5$ (c 0.79, CHCl$_3$), chiral HPLC analysis (Chiralcel OD-H, 250×4.6 mm, 2% ethanol/hexane; 1.2 ml/min), 94.8% e.e.

Example 6

Preparation of 1-(4-acetoxyphenyl)-2-(p-tolylsulfonyloxy)ethanol 0.174 g (0.5 mmol) of 1-(4-acetoxyphenyl)-2-(p-tolylsulfonyloxy)ethanone and 0.4 mg (0.0005 mmol) of [S,S]-TsD-PEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.1 ml of a mixture of formic acid and triethyamine (5:2, molar ratio) was added thereto. The resulting mixture was stirred at room temperature for 2 hrs and washed with water, and the combined organic layer was dried over anhydrous sodiumsulfate and filtered. The residue was subjected to a column chromatography to obtain the title compound (yield: 94%).

$^1$H NMR (300 MHz; CDCl$_3$) δ 7.77 (2H, d, J=8.4 Hz), 7.36-7.32 (4H, m), 7.06 (2H, d, J=8.6 Hz), 4.99 (1H, dd, J=8.5 and 3.2 Hz), 4.12 (1H, dd, J=10.4 and 3.4 Hz), 4.01 (1H, dd, J=10.4 and 8.7 Hz), 2.61 (1H, d, J=3.2 Hz), 2.45 (3H, s) 2.30 (3H, s), $^{13}$C NMR (CDCl$_3$) δ 169.41, 150.63, 145.14, 135.79, 132.44, 129.96, 127.94, 127.32, 121.82, 74.18, 71.37, 21.64, 21.08, EIMS (70 eV) m/z (relative intensity) 165 (M$^+$-CH$_2$OTs, 39), 123 (100), 91 (17); $[\alpha]_D^{29}$-41.20 (c 1.085 g, CHCl$_3$), chiral HPLC analysis (Chiralcel OD-H, 250×4.6 mm, 5% ethanol/hexane; 0.5 ml/min), 95.5% e.e.

Example 7

Preparation of 1-(4-tert-butyldimethylsilyloxyphenyl)-2-(p-tolylsulfonyloxy)ethanol 0.420 g (0.1 mmol) of 1-(4-tert-butyldimethylsilyloxyphenyl)-2-(p-tolylsulfonyloxy)ethanone and 0.7 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 2 hrs and washed with water, and the combined organic layer was dried over anhydrous sodiumsulfate and filtered. The obtained residue was subjected to a column chromatography to obtain the title compound (yield: 60%).

$^1$H NMR (300 MHz; CDCl$_3$) δ 7.78 (2H, d, J=8.3 Hz), 7.34 (2H, d, J=8.0 Hz), 7.16 (2H, d, J=8.3 Hz), 6.79 (2H, d, J=8.6 Hz), 4.92-4.90 (1H, m), 4.11 (1H, dd, J=10.4 and 3.4 Hz), 4.02 (1H, dd, J=10.4 and 8.6 Hz), 2.45 (3H, s) 0.97 (9H, s), 0.18 (6H, s), $^{13}$C NMR (CDCl$_3$) δ 155.92, 145.03, 132.67, 130.82, 129.92, 127.93, 127.40, 120.23, 74.32, 71.57, 25.62, 21.65, 18.16, −4.46;

EIMS (70 eV) m/z (relative intensity) 422 (M$^+$, 1) 237 (100), 193 (19), 149 (12), 91 (14), $[\alpha]_D^{29}$−37.35 (c 1.02 g, CHCl$_3$), chiral HPLC analysis (Chiralcel OD-H, 250×4.6 mm, 1% ethanol/hexane; 0.4 ml/min), 96.0% e.e.

Example 8

Preparation of (R)-(−)-1-(2-chlorophenyl)-2-(p-tolylsulfonyloxy)ethanol 324 mg (1 mmol) of 1-(2-chlorophenyl)-2-(p-tolylsulfonyloxy)ethanone and 0.8 mg (0.001 mmol) of [S,S]-TsDPEN-RhCl-Cp*/Et$_3$N.HCl obtained in Preparation Example 1 were placed in a 10 ml round flask, and the flask was sealed. After introducing argon gas therein for 10 mins, 2.5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 24 hrs and subjected to a column chromatography to obtain the title compound (yield: 42%).

$[\alpha]_D^{25}$=−42.1 (c=0.98, CHCl$_3$), 61.8% e.e., $^1$H NMR (300 MHz, CDCl$_3$) δ 7.78 (d, 2H, J=8.1), 7.58 (d, 1H, J=7.8), 7.34-7.23 (m, 5H), 5.37-5.33 (m, 1H), 4.27 (dd, 1H, J=2.7, 10.8), 4.02-3.95 (m, 1H), 2.45 (s, 3H).

Example 9

Preparation of (R)-(−)-1-(3-chlorophenyl)-2-(p-tolylsulfonyloxy)ethanol 324 mg (1 mmol) of 1-(3-chlorophenyl)-2-(p-tolylsulfonyloxy)ethanone and 0.8 mg (0.001 mmol) of [S,S]-TsDPEN-RhCl-Cp*/Et$_3$N.HCl obtained in Preparation Example 1 were placed in a 10 ml round flask, and the flask was sealed. After introducing argon gas therein for 10 mins, 2.5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 99%).

$[\alpha]_D^{25}$=−37.8 (c=2.45, CHCl$_3$), 94.7% e.e., $^1$H NMR (300 MHz, CDCl$_3$) δ 7.76 (d, 2H, J=8.1), 7.35-7.18 (m, 6H), 4.99-4.94 (m, 1H), 4.16-3.99 (m, 2H), 2.46 (s, 3H).

Example 10

Preparation of (R)-(−)-1-(4-chlorophenyl)-2-(p-tolylsulfonyloxy)ethanol 324 mg (1 mmol) of 1-(4-chlorophenyl)-2-(p-tolylsulfonyloxy)ethanone and 0.8 mg (0.001 mmol) of [S,S]-TsDPEN-RhCl-Cp*/Et$_3$N.HCl obtained in Preparation Example 1 were placed in a 10 ml round flask, and the flask was sealed. After introducing argon gas therein for 10 mins, 2.5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 94%).

$[\alpha]_D^{25}$=−44.8 (c=2.52, CHCl$_3$), 92.0% e.e., $^1$H NMR (300 MHz, CDCl$_3$) δ 7.75 (d, 2H, J=8.1), 7.35-7.23 (m, 6H), 4.99-4.94 (m, 1H), 4.15-3.99 (m, 2H), 2.45 (s, 3H).

Example 11

Preparation of (R)-(−)-1-(4-nitrophenyl)-2-(p-tolylsulfonyloxy)ethanol 335 mg (1 mmol) of 1-(4-nitrophenyl)-2-(p-tolylsulfonyloxy)ethanone and 0.8 mg (0.001 mmol) of [S,S]-TsDPEN-RhCl-Cp*/Et$_3$N.HCl obtained in Preparation Example 1 were placed in a 10 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 95%).

$[\alpha]_D^{25}$=−23.6 (c=1.06, acetone), 68.9% e.e., $^1$H NMR (300 MHz, CDCl$_3$) δ 8.19 (d, 2H, J=8.6), 7.75 (d, 2H, J=8.1), 7.52 (d, 2H, J=8.5), 7.33 (d, 2H, J=8.0), 5.12-5.10 (m, 1H), 4.22-4.04 (m, 2H), 2.45 (s, 3H).

Example 12

Preparation of (R)-(−)-1-(4-methoxy-3-nitrophenyl)-2-(p-tolylsulfonyloxy)ethanol 320 mg (1 mmol) of 1-(4-methoxy-3-nitrophenyl)-2-(p-tolylsulfonyloxy)ethanone and 0.8 mg (0.001 mmol) of [S,S]-

TsDPEN-RhCl-Cp*/Et₃N.HCl obtained in Preparation Example 1 were placed in a 10 ml round flask, and the flask was sealed. After introducing argon gas therein for 10 mins, 6 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 3 hrs and subjected to a column chromatography to obtain the title compound (yield: 98%).

$[\alpha]_D^{25}$=−36.3 (c=2.49, CHCl₃), 84.4% e.e.,

¹H NMR (300 MHz, CDCl₃) δ 7.78 (s, 1H), 7.75 (d, 2H, J=8.4), 7.54 (d, 1H, J=8.4), 7.34 (d, 2H, J=8.1), 7.06 (d, 1H, J=8.7), 5.00-4.98 (m, 1H), 4.16-4.00 (m, 2H), 2.46 (s, 3H).

Example 13

Preparation of (R)-(−)-1-(naphthalen-2-yl)-2-(p-tolylsulfonyloxy)ethanol 340 mg (1 mmol) of 1-(naphthalen-2-yl)-2-(p-tolylsulfonyloxy)ethanone and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 3 hrs and subjected to a column chromatography to obtain the title compound (yield: 98%).

$[\alpha]_D^{25}$=−49.0 (c=2.50, CHCl₃), 91.8% e.e.,

¹H NMR (300 MHz, CDCl₃) δ 7.83-7.72 (m, 6H), 7.51-7.47 (m, 2H), 7.38 (d, 1H, J=8.7), 7.27-7.25 (m, 2H), 5.15 (dd, 1H, J=3.3, 8.1), 4.27-4.11 (m, 2H), 2.45 (s, 3H).

Example 14

Preparation of (R)-(−)-2-hydroxy-5-[1-hydroxy-2-(p-tolylsulfonyloxy)ethyl]benzoic acid methylester 364 mg (1 mmol) of 2-hydroxy-5-[2-(p-tolylsulfonyloxy)acetyl]benzoic acid methylester and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 10 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 6 hrs and subjected to a column chromatography to obtain the title compound (yield: 52%).

$[\alpha]_D^{25}$=−3.8 (c=1.43, CHCl₃), 9.8% e.e.,

¹H NMR (300 MHz, CDCl₃) δ 10.75 (s, 1H), 7.80-7.74 (m, 3H), 7.40-7.31 (m, 3H), 6.94 (d, 1H, J=8.4), 4.95-4.91 (m, 1H), 4.14-4.03 (m, 2H), 3.59 (s, 3H), 2.45 (s, 3H).

Example 15

Preparation of (R)-(−)-1-(2,3-dihydro-benzo[1,4]dioxin-6-yl)-2-(p-tolylsulfonyloxy)ethanol 348 mg (1 mmol) of 1-(2,3-dihydro-benzo[1,4]dioxin-6-yl)-2-(p-tolylsulfonyloxy)ethanone and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 5 hrs and subjected to a column chromatography to obtain the title compound (yield: 94%).

$[\alpha]_D^{25}$=−36.9 (c=1.73, CHCl₃),

¹H NMR (300 MHz, CDCl₃) δ 7.78 (d, 2H, J=8.4), 7.34 (d, 2H, J=8.1), 6.83-6.74 (m, 3H), 4.86 (dd, 1H, J=3.6, 8.6), 4.23 (s, 4H), 4.12-3.97 (m, 2H), 2.45 (s, 3H).

Example 16

Preparation of (R)-(−)-1-(2-bromophenyl)-2-(p-tolylsulfonyloxy)ethanol 369 mg (1 mmol) of 1-(2-bromophenyl)-2-(p-tolylsulfonyloxy)ethanone and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 24 hrs and subjected to a column chromatography to obtain the title compound (yield: 12%).

$[\alpha]_D^{25}$=−37.7 (c=0.28, CHCl₃), 84.9% e.e.,

¹H NMR (300 MHz, CDCl₃) δ 7.78 (d, 2H, J=8.3), 7.57 (d, 1H, J=7.7), 7.47 (d, 1H, J=7.9), 7.34-7.30 (m, 3H), 7.17 (t, 1H, J=7.7), 5.31-5.29 (m, 1H), 4.27 (dd, 1H, J=2.6, 10.5), 4.00-3.94 (m, 1H), 2.44 (s, 3H).

Example 17

Preparation of (R)-(−)-1-(3-trifluoromethylphenyl)-2-(p-tolylsulfonyloxy)ethanol 358 mg (1 mmol) of 1-(3-trifluoromethylphenyl)-2-(p-tolylsulfonyloxy)ethanone and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 96%).

$[\alpha]_D^{25}$=−31.6 (c=2.42 CHCl₃), 88.1% e.e.,

¹H NMR (300 MHz, CDCl₃) δ 7.74 (d, 2H, J=8.4), 7.58-7.43 (m, 4H), 7.33 (d, 2H, J=8.1), 5.07-5.02 (m, 1H), 4.19-4.02 (m, 2H), 2.44 (s, 3H).

Example 18

Preparation of (R)-(−)-1-(4-methylphenyl)-2-(p-tolylsulfonyloxy)ethanol 304 mg (1 mmol) of 1-(4-methylphenyl)-2-(p-tolylsulfonyloxy)ethanone and 0.8 mg (0.001 mmol) of [S,S]-TsDPEN-RhCl-Cp*/Et₃N.HCl obtained in Preparation Example 1 were, placed in a 10 ml round flask, and the flask was sealed. After introducing argon gas therein for 10 mins, 2 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 97%).

$[\alpha]_D^{25}$=−47.8 (c=1.27, CHCl₃),
98.0% e.e.,
¹H NMR (500 MHz, CDCl₃) δ 7.76 (d, 2H, J=8.3), 7.32 (d, 2H, J=8.0), 7.19 (d, 2H, J=8.0), 7.14 (d, 2H, J=7.7), 4.94-4.92 (m, 1H), 4.13-4.01 (m, 2H), 2.44 (s, 3H), 2.33 (s, 3H).

Example 19

Preparation of (R)-(−)-1-(4-fluorophenyl)-2-(p-tolylsulfonyloxy)ethanol 308 mg (1 mmol) of 1-(4-fluorophenyl)-2-(p-tolylsulfonyloxy)ethanone and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 2 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 0.5 hr and subjected to a column chromatography to obtain the title compound (yield: 98%).

$[\alpha]_D^{25}$=−34.8 (c=1.59, CHCl₃),
92.7% e.e.,
¹H NMR (300 MHz, CDCl₃) δ 7.76 (d, 2H, J=8.2), 7.35-7.28 (m, 4H), 7.01 (t, 2H, J=8.6), 4.99-4.94 (m, 1H), 4.14-3.99 (m, 2H), 2.45 (s, 3H).

Example 20

Preparation of (R)-(−)-1-(3,4-dimethoxyphenyl)-2-(p-tolylsulfonyloxy)ethanol 320 mg (1 mmol) of 1-(3,4-dimethoxyphenyl)-2-(p-tolylsulfonyloxy)ethanone and 0.8 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 2 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 8 hrs and subjected to a column chromatography to obtain the title compound (yield: 94%).

$[\alpha]_D^{25}$=−27.0 (c=0.83, CHCl₃),
89.9% e.e.,
¹H NMR (300 MHz, CDCl₃) δ 7.32 (d, 2H, J=8.2), 7.75 (d, 2H, J=8.3), 6.85-6.82 (m, 3H), 4.94-4.90 (m, 1H), 4.14-4.02 (m, 2H), 3.86 (s, 3H), 3.84 (s, 3H), 2.44 (s, 3H).

Example 21

Preparation of (R)-(−)-1-(2-methoxy-5-methylphenyl)-2-(p-tolylsulfonyloxy)ethanol 290 mg (0.86 mmol) of 1-(2-methoxy-5-methylphenyl)-2-(p-tolylsulfonyloxy)ethanone and 0.7 mg (0.001 mmol) of [S,S]-TsDPEN-RhCl-Cp*/Et₃N.HCl obtained in Preparation Example 1 were placed in a 10 ml round flask, and the flask was sealed. After introducing argon gas therein for 10 mins, 2 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 3 days and subjected to a column chromatography to obtain the title compound (yield: 77%).

$[\alpha]_D^{25}$=−32.7 (c=0.65, CHCl₃),
89.6% e.e. (this value was determined after converting the product to the acetate form),
¹H NMR (300 MHz, CDCl₃) δ 7.76 (2H, d, J=8.3 Hz), 7.32 (2H, d, J=8.0 Hz), 7.15 (1H, d, J=1.9 Hz), 7.05 (1H, dd, J=8.7 and 1.7 Hz), 6.71 (1H, d, J=8.3 Hz), 5.15-5.10 (1H, m), 4.25 (1H, dd, J=10.1 and 3.4 Hz), 4.05 (1H, dd, J=10.1 and 8.1 Hz), 3.73 (3H, s), 2.82 (1H, d, J=5.3 Hz), 2.44 (3H, s), 2.26 (3H, s).

Example 22

Preparation of (R)-2-(methanesulfonyloxy)-1-phenylethanol 0.214 g (1 mmol) of 2-(methanesulfonyloxy)-1-phenylethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 98%).

$[\alpha]_D^{29}$=−50.3 (c 1.10, CHCl₃),
97.30% e.e.,
¹H NMR (300 MHz, CDCl₃) δ 7.39-7.30 (5H, m), 5.03-4.98 (1H, m), 4.31 (1H, dd, J=10.8 and 3.7 Hz), 4.25 (1H, dd, J=10.8 and 7.8 Hz), 3.15 (1H, d, J=3.4 Hz), 2.99 (3H, s).

Example 23

Preparation of (R)-1-(2-chlorophenyl)-2-(methanesulfonyloxy)ethanol 0.248 g (1 mmol) of 1-(2-chlorophenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed.

After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 90%).

$[\alpha]_D^{28}$=−53.2 (c 1.03, CHCl$_3$), 76.80% e.e., $^1$H NMR (300 MHz, CDCl$_3$) δ 7.64 (1H, d, J=8.2 Hz), 7.37-7.24 (3H, m), 5.45-5.42 (1H, m), 4.44 (1H, dd, J=10.9 and 2.6 Hz), 4.22 (1H, dd, J=10.9 and 8.1 Hz), 3.22 (1H, d, J=3.0 Hz), 3.06 (3H, s).

Example 24

Preparation of (R)-1-(3-chlorophenyl)-2-(methanesulfonyloxy)ethanol 0.248 g (1 mmol) of 1-(3-chlorophenyl)-2-(methanesulfonyloxy)ethanone and 0.8 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 95%).

$[\alpha]_D^{28}$=−39.0 (c 1.02, CHCl$_3$), 96.44% e.e., $^1$H NMR (300 MHz, CDCl$_3$) δ 7.41 (1H, s), 7.32-7.24 (3H, m), 5.04-4.99 (1H, m), 4.32 (1H, dd, J=10.9 and 3.4 Hz), 4.24 (1H, dd, J=10.8 and 8.0 Hz), 3.24 (1H, d, J=3.1 Hz), 3.04 (3H, s).

Example 25

Preparation of (R)-1-(4-chlorophenyl)-2-(methanesulfonyloxy)ethanol 0.248 g (1 mmol) of 1-(4-chlorophenyl)-2-(methanesulfonyloxy)ethanone and 0.8 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 97%).

$[\alpha]_D^{28}$=−44.7 (c 1.02, CHCl$_3$), 95.20% e.e., $^1$H NMR (300 MHz, CDCl$_3$) δ 7.37-7.31 (4H, m), 5.04-4.99 (1H, m), 4.30 (1H, dd, J=10.8 and 3.5 Hz), 4.23 (1H, dd, J=10.8 and 8.0 Hz), 3.08 (1H, d, 1=3.5 Hz), 3.04 (3H, s).

Example 26

Preparation of (R)-1-(2-methoxyphenyl)-2-(methanesulfonyloxy)ethanol 0.244 g (1 mmol) of 1-(2-methoxyphenyl)-2-(methanesulfonyloxy)ethanone and 0.8 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.4 ml of a mixture of formic acid and triethyamine (5:2, molar ratio) was added thereto. The resulting mixture was stirred at room temperature for 24 hrs and subjected to a column chromatography to obtain the title compound (yield: 92%).

$[\alpha]_D^{28}$=−50.11 (c 1.13, CHCl$_3$), 88.23% e.e., $^1$H NMR (300 MHz, CDCl$_3$) δ 7.43 (1H, d, J=7.5 Hz), 7.31 (1H, t, J=7.9 Hz), 7.00 (1H, t, J=7.5 Hz), 6.89 (1H, d, J™ 8.2 Hz), 5.25 (1H, dd, J=8.0 and 3.1 Hz), 4.43 (1H, dd, J=10.7 and 3.1 Hz), 4.31 (1H, dd, J=10.7 and 8.0 Hz), 3.85 (3H, s), 3.02 (3H, s).

Example 27

Preparation of (R)-1-(3-methoxyphenyl)-2-(methanesulfonyloxy)ethanol 0.244 g (1 mmol) of 1-(3-methoxyphenyl)-2-(methanesulfonyloxy)ethanone and 0.8 mg (0.001 mmol) of [8,5]-TsDPEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 97%).

$[\alpha]_D^{28}$=−38.9 (c 1.12, CHCl$_3$), 96.73% e.e., $^1$H NMR (300 MHz, CDCl$_3$) δ 7.27 (1H, t, J=8.2 Hz), 6.95-6.83 (3H, m), 5.00-4.96 (1H, m), 4.31 (1H, dd, J=10.8 and 3.6 Hz), 4.25 (1H, dd, J=10.8 and 8.0 Hz), 3.79 (3H, s), 3.20 (1H, d, J=3.5 Hz), 3.01 (3H, s).

Example 28

Preparation of (R)-1-(4-methoxyphenyl)-2-(methanesulfonyloxy)ethanol 0.244 g (1 mmol) of 4-methoxyphenyl)-2-(methanesulfonyloxy)ethanone and 0.8 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 5 ml of ethylacetate was added thereto to completely dissolve the starting materials, and 0.4 ml of a mixture of formic acid and triethyamine (5:2, molar ratio) was added thereto. The resulting mixture was stirred at room temperature for 4 hrs and subjected to a column chromatography to obtain the title compound (yield: 93%).

$[\alpha]_D^{25}$=−51.0 (c 1.09, CHCl$_3$), 97.24% e.e., $^1$H NMR (300 MHz, CDCl$_3$) δ 7.31 (2H, d, J=8.7 Hz), 6.91 (2H, d, J=8.4 Hz), 4.99 (1H, dd, J=7.5 and 4.5 Hz), 4.30 (1H, dd, J=11.1 and 4.5 Hz), 4.26-4.23 (1H, m), 3.81 (3H, s), 3.04 (3H, s).

Example 29

Preparation of (R)-2-(methanesulfonyloxy)-1-(naphthalene-2-yl)ethanol 0.264 g (1 mmol) of 2-(methanesulfonyloxy)-1-(naphthalene-2-yl)ethanone and 0.8 mg (0.001 mmol) of [S,S]-TsD- PEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 96%).

$[\alpha]_D^{28}$=−51.4 (c 0.53, CHCl₃),
99.27% e.e.,
¹H NMR (300 MHz, CDCl₃) δ 7.88-7.83 (4H, m), 7.52-7.46 (3H, m), 5.24-5.19 (1H, m), 4.44 (1H, dd, J=11.0 and 3.7 Hz), 4.37 (1H, dd, J=10.9 and 8.0 Hz), 3.04 (3H, s), 2.87 (1H, d, J=3.4 Hz).

Example 30

Preparation of (R)-1-(4-tert-butylphenyl)-2-(methanesulfonyloxy)ethanol 0.270 g (1 mmol) of 1-(4-tent-butylphenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 2 hrs and subjected to a column chromatography to obtain the title compound (yield: 85%).

$[\alpha]_D^{25}$=−47.9 (c 0.98, CHCl₃),
98.98% e.e.,
¹H NMR (300 MHz, CDCl₃) δ 7.41 (2H, d, J=8.4 Hz), 7.32 (2H, d, J=8.3 Hz), 5.02 (1H, dd, J=7.5 and 3.7 Hz), 4.34-4.31 (1H, m), 4.28 (1H, dd, J=10.9 and 7.8 Hz), 3.03 (3H, s), 1.31 (9H, s).

Example 31

Preparation of (R)-1-(4-acetoxyphenyl)-2-(methanesulfonyloxy)ethanol 0.272 g (1 mmol) of 1-(4-acetoxyphenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 97%).

$[\alpha]_D^{26}$=−41.3 (c 1.05, CHCl₃),
97.42% e.e.,
¹H NMR (300 MHz, CDCl₃) δ 7.41 (2H, d, J=8.6 Hz), 7.10 (2H, d, J=8.47 Hz), 5.03-5.00 (1H, m), 4.31 (1H, dd, J=10.8 and 3.5 Hz), 4.24 (1H, dd, J=10.3 and 8.0 Hz), 3.02 (3H, s), 2.93 (1H, d, J=3.1 Hz), 2.30 (3H, s).

Example 32

Preparation of (R)-1-(4-tert-butyl-di-methylsilylphenyl)-2-(methanesulfonyloxy)ethanol 0.344 g (1 mmol) of 1-(4-tert-butyl-di-methylsilylphenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 68%).

$[\alpha]_D^{26}$=−35.2 (c 1.02, CHCl₃),
97.64% e.e.,
¹H NMR (300 MHz, CDCl₃) δ 7.06 (2H, d, J=8.5 Hz), 6.65 (2H, d, J=8.0 Hz), 4.80-4.77 (1H, m), 4.12-4.06 (2H, m), 2.84 (3H, s), 2.40 (1H, s), 0.75 (9H, s), 0.00 (6H, s).

Example 33

Preparation of (R)-2-(methanesulfonyloxy)-1-(3-trifluoromethylphenyl)ethanol 0.282 g (1 mmol) of 2-(methanesulfonyloxy)-1-(3-trifluoromethylphenyl)ethanone and 0.8 mg (0.001 mmol) of [S,5]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 91%).

$[\alpha]_D^{28}$=−33.3 (c 1.10, CHCl₃),
94.12% e.e.,
¹H NMR (300 MHz, CDCl₃) δ 7.69 (1H, s), 7.59 (2H, d, J=7.4 Hz), 7.51 (1H, t, J=7.5 Hz), 5.12-5.09 (1H, m), 4.35 (1H, dd, J=10.9 and 3.4 Hz), 4.26 (1H, dd, J=10.9 and 8.0 Hz), 3.43 (1H, d, J=2.8 Hz), 3.04 (3H, s).

Example 34

Preparation of (R)-2-(methanesulfonyloxy)-1-(4-trifluoromethylphenyl)ethanol 0.282 g (1 mmol) of 2-(methanesulfonyloxy)-1-(4-trifluoromethylphenyl)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 20 mins and subjected to a column chromatography to obtain the title compound (yield: 98%).

$[\alpha]_D^{25}$=−37.7 (c 1.16, CHCl₃),
95.87% e.e.,
¹H NMR (300 MHz, CDCl₃) δ 7.66 (2H, d, J=8.1 Hz), 7.54 (2H, d, J=8.1 Hz), 5.14-5.11 (1H, m), 4.36 (1H, dd, J=10.8 and 3.3 Hz), 4.27 (1H, dd, J=11.1 and 8.1 Hz), 3.06 (3H, s), 2.88 (1H, d, J=3.6 Hz).

Example 35

Preparation of (R)-1-(4-fluorophenyl)-2-(methanesulfonyloxy)ethanol 0.232 g (1 mmol) of 1-(4-fluorophenyl)-2-(methanesulfonyloxy)ethanone and 0.8 mg (0.001 mmol) of [S,S]-TsD- PEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 94%).

$[\alpha]_D^{28}$=−47.1 (c 1.05, CHCl₃),
96.23% e.e.,
¹H NMR (300 MHz, CDCl₃) δ 7.41-7.34 (2H, m), 8.07 (2H, t, J=8.7 Hz), 5.06-5.01 (1H, m), 4.31 (1H, dd, J=10.9 and 3.7 Hz), 4.24 (1H, dd, J=10.9 and 8.0 Hz), 3.04 (3H, s), 2.96 (1H, d, J=3.4 Hz).

Example 36

Preparation of (R)-1-(3,4-di-chlorophenyl)-2-(methanesulfonyloxy)ethanol 0.283 g (1 mmol) of 1-(3,4-dichlorophenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 1 hr and subjected to a column chromatography to obtain the title compound (yield: 99%).

$[\alpha]_D^{25}$=−37.5 (c 0.97, CHCl₃),
93.79% e.e.,
¹H NMR (300 MHz, CDCl₃) δ 7.52 (1H, d, J=1.7 Hz), 7.46 (1H, d, J=8.3 Hz), 7.26 (1H, dd, J=8.3 and 1.7 Hz), 5.03-5.00 (1H, m), 4.32 (11-1, dd, J=10.9 and 3.3 Hz), 4.22 (1H, dd, J=10.9 and 8.2 Hz), 3.06 (3H, s), 2.95 (1H, s).

Example 37

Preparation of (R)-2-(methanesulfonyloxy)-1-(4-nitrophenyl)ethanol 0.130 g (0.5 mmol) of 2-(methanesulfonyloxy)-1-(4-nitrophenyl)ethanone and 0.4 mg (0.0005 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.1 ml of a mixture of formic acid and triethyamine (5:2, molar ratio) was added thereto. The resulting mixture was stirred at room temperature for 40 mins and subjected to a column chromatography to obtain the title compound (yield: 90%).

$[\alpha]_D^{28}$=−35.9 (c 0.51, Acetone),
87.59% e.e.,
¹H NMR (300 MHz, DMSO-d₆) δ 8.22 (2H, d, J=8.6 Hz), 7.69 (2H, d, J=8.8 Hz), 5.04-5.00 (1H, m), 4.30 (1H, dd, J=10.4 and 4.0 Hz), 4.24 (1H, dd, J=10.4 and 6.4 Hz), 3.12 (3H, s).

Example 38

Preparation of (R)-1-(1,4-benzodioxan-6-yl)-2-(methanesulfonyloxy)ethanol 0.272 g (1 mmol) of 1-(1,4-benzodioxan-6-yl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 2 hrs and subjected to a column chromatography to obtain the title compound (yield: 92%).

$[\alpha]_D^{26}$=−41.9 (c 1.21, CHCl₃),
97.32% e.e.,
¹H NMR (300 MHz, CDCl₃) δ 6.90-6.85 (3H, m), 4.92 (1H, dd, J=7.8 and 3.8 Hz), 4.29-4.22 (6H, m), 3.04 (3H, s).

Example 39

Preparation of (R)-1-(2-methoxy-5-methylphenyl)-2-(methanesulfonyloxy)ethanol 0.258 g (1 mmol) of 1-(2-methoxy-5-methylphenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.4 ml of a mixture of formic acid and triethyamine (5:2, molar ratio) was added thereto. The resulting mixture was stirred at room temperature for 19 hrs and subjected to a column chromatography to obtain the title compound (yield: 91%).

$[\alpha]_D^{28}$=−42.1 (c 1.21, CHCl₃),
89.57% e.e.,
¹H NMR (300 MHz, CDCl₃) δ 7.22 (1H, d, J=1.9 Hz), 7.09 (1H, dd, J=8.3 and 2.0 Hz), 6.78 (1H, d, J=8.3 Hz), 5.21 (1H, dd, J=8.1 and 3.1 Hz), 4.40 (1H, J=10.6 and 3.0 Hz), 4.30 (1H, dd, J=10.7 and 8.1 Hz), 3.82 (3H, s), 3.03 (3H, s), 2.73 (1H, s), 2.29 (3H, s).

Example 40

Preparation of (R)-1-(4-methoxy-3-nitrophenyl)-2-(methanesulfonyloxy)ethanol 0.289 g (1 mmol) of 1-(4-methoxy-3-nitrophenyl)-2-(methanesulfonyloxy)ethanone and 0.8 mg (0.001 mmol) of [S,S]-TsDPEN-RhCl-Cp*/Et₃N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 90%).

$[\alpha]_D^{26}$=−41.6 (c 1.04, CHCl₃),
92.00% e.e.,
¹H NMR (300 MHz, CDCl₃) δ 7.91 (1H, d, J=2.1 Hz), 7.59 (1H, dd, J=8.7 and 2.2 Hz), 7.12 (1H, d, J=8.7 Hz), 5.07-5.05 (1H, m), 4.33 (1H, dd, J=10.9 and 3.3 Hz), 4.25 (1H, dd, J=10.9 and 8.0 Hz), 3.97 (3H, s), 3.08 (3H, s).

Example 41

(R)-1-(4-methoxy-3-methoxymethylphenyl)-2-(methanesulfonyloxy)ethanol 0.288 g (1 mmol) of 1-(4-methoxy-3-methoxymethylphenyl)-2-(methanesulfonyloxy)ethanone and 0.8 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 4 hrs and subjected to a column chromatography to obtain the title compound (yield: 93%).

$[\alpha]_D^{25}$=−41.5 (c 1.86, CHCl$_3$),
95.40% e.e.,
$^1$H NMR (300 MHz, CDCl$_3$) δ 7.38 (1H, d, J=1.8 Hz), 7.30 (1H, d, J=8.4 and 2.1 Hz), 6.87 (1H, d, J=8.4 Hz), 4.99 (1H, dd, J=6.6 and 4.8 Hz), 4.48 (2H, s), 4.31-4.27 (2H, m), 3.84 (2H, s), 3.43 (3H, s), 3.04 (3H, s).

Example 42

Preparation of (R)-1-(4-N,N'-bis(methanesulfonyl) aminophenyl)-2-(methanesulfonyloxy)ethanol 0.385 g (1 mmol) of 1-(4-N,N'-bis(methanesulfonyl)aminophenyl)-2-(methanesulfonyloxy)ethanone and 0.8 mg (0.001 mmol) of [S,S]-TsDPEN-RhCl-Cp*/Et$_3$N.HCl obtained in Preparation Example 1 were placed in a 25 ml round flask, and the flask was sealed. After introducing argon gas therein for 10 mins, 5 ml of ethylacetate was added thereto to completely dissolve the starting materials, and 0.4 ml of a mixture of formic acid and triethyamine (5:2, molar ratio) was added thereto. The resulting mixture was stirred at room temperature for 48 hrs and subjected to a column chromatography to obtain the title compound (yield: 50%).

$[\alpha]_D^{26}$=−0.52, Acetone),
96.5% e.e.,
$^1$H NMR (300 MHz, Acetone) δ 7.61 (2H, d, J=8.4 HZ), 7.51 (2H, d, J=8.4 Hz), 5.16-5.09 (1H, m), 4.36 (1H, dd, J=10.5 and 3.6 Hz), 4.29 (1H, dd, J=10.5 and 7.0 Hz), 3.49 (6H, s), 3.05 (3H, s), 2.86 (1H, s).

Example 43

Preparation of (S)-2-chloro-1-phenylethanol 155 mg (1 mmol) of 2-chloro-1-phenylethanone and 1.5 mg (0.002 mmol) of [R,R]-TsDPEN-RhCl-Cp*/Et$_3$N.HCl obtained in Preparation Example 2 were placed in a 10 ml round flask, and the flask was sealed. After introducing argon gas therein for 10 mins, 1 ml of ethylacetate was added thereto to completely dissolve the starting materials, and 0.2 ml of a mixture of formic acid and triethyamine (5:2, molar ratio) was added thereto. After 2 hrs, the reaction mixture was directly loaded on a silica gel (200 mesh) column using 15% EtOAc/hexane as an eluent to obtain 150 mg of the title compound as an liquid (yield: 96%).

$[\alpha]_D^{25}$=+42.8 (c=3.88, C$_6$H$_{12}$),
HPLC analysis (Chiralcel OD-H, 250×4.6 mm, hexane:ethanol=95:5, 0.5 ml/min): e.e.=96.3%,
$^1$H NMR (300 MHz, CDCl$_3$) δ 7.39-7.29 (5H, m); 4.92 (1H, d, J=5.7 Hz); 3.72 (1H, dd, J=11.4 and 3.6 Hz); 3.68 (1H, dd, J=8.7 and 2.4 Hz); 2.64 (OH, d, J=2.7 Hz).

Example 44

Preparation of (S)-2-bromo-1-phenylethanol 199 mg (1 mmol) of 2-bromo-1-phenylethanone and 1.5 mg (0.002 mmol) of [R,R]-TsDPEN-RhCl-Cp*/Et$_3$N.HCl obtained in Preparation Example 2 were placed in a 10 ml round flask, and the flask was sealed. After introducing argon gas therein for 10 mins, 1 ml of ethylacetate was added thereto to completely dissolve the starting materials, and 0.2 ml of a mixture of formic acid and triethyamine (5:2, molar ratio) was added thereto. After 24 hrs, the reaction mixture was directly loaded on a silica gel (200 mesh) column using 0-10% (gradient) EtOAc/hexane as an eluent to obtain 106 mg of the title compound as an liquid (yield: 53%).

$[\alpha]_D^{25}$=+13.9 (c=1.34, CHCl$_3$),
HPLC analysis (Chiralcel OD-H, 250×4.6 mm, hexane:ethanol=95:5, 0.5 ml/min): e.e.=28.3%,
$^1$H NMR (300 MHz, CDCl$_3$) δ 7.39-7.29 (5H, m); 4.95 (1H, m); 3.66 (1H, dd, J=10.4 and 3.3 Hz); 3.57 (1H, dd, J=10.4 and 8.8 Hz); 2.63 (OH, d, J=3 Hz).

Example 45

Preparation of (S)-(+)-1-phenyl-2-(p-tolylsulfonyloxy)ethanol 290 mg (1 mmol) of 1-phenyl-2-(p-tolylsulfonyloxy)ethanone and 0.8 mg (0.001 mmol) of [R,R]-TsDPEN-RhCl-Cp*/Et$_3$N.HCl obtained in Preparation Example 2 were placed in a 10 ml round flask, and the flask was sealed. After introducing argon gas therein for 10 mins, 2.5 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 4 hrs and subjected to a column chromatography to obtain the title compound (yield: 97%).

$[\alpha]_D^{25}$=+51.2 (c=2.02, CHCl$_3$),
chiral HPLC: 95.2% e.e.,
$^1$H NMR (300 MHz, CDCl$_3$) δ 7.78 (2H, d, J=8.4 Hz); 7.36-7.27 (7H, m); 4.99 (1H, d, J=8.7 Hz); 4.17 (1H, dd, J=10.2 and 3.3 Hz); 4.07 (1H, dd, J=10.2 and 8.7 Hz); 2.55 (OH, d, J=3 Hz); 2.44 (3H, s).

Example 46

Preparation of (S)-(+)-1-(4-methoxyphenyl)-2-(p-tolylsulfonyloxy)ethanol 1.602 g (5 mmol) of 1-(4-methoxyphenyl)-2-(p-tolylsulfonyloxy)ethanone and 3.89 mg (0.005 mmol) of [R,R]-TsDPEN-RhCl-Cp*/Et$_3$N.HCl obtained in Preparation Example 2 were placed in a 10 ml round flask, and the flask was sealed. After introducing argon gas therein for 10 mins, 35 ml of ethylacetate was added thereto to completely dissolve the starting materials, and 1 ml of a mixture of formic acid and triethylamine (5:2, molar ratio) were added thereto. When the color of the reaction mixture changed from light yellow to dark red after 2 to 3 mins, the reaction mixture was stirred at room temperature for 18 hrs and subjected to a column chromatography to obtain the title compound (yield: 94%).

$[\alpha]_D^{25}$=+49.3 (c=2.46, CHCl$_3$),
94.4% e.e.,
$^1$H NMR (300 MHz, CDCl$_3$) δ 7.77 (d, 2H, J=8.4), 7.33 (d, 2H, J=8.1), 7.23 (d, 2H, J=7.2), 6.86 (d, 2H, J=8.7), 4.92 (dd, 1H, J=3.5, 8.4), 4.13-4.00 (m, 2H), 3.79 (s, 3H), 2.45 (s, 3H).

Example 47

Preparation of (S)-(+)-1-(4-chlorophenyl)-2-(p-tolylsulfonyloxy)ethanol 324 mg (1 mmol) of 1-(4-chlorophenyl)-2-(p-tolylsulfonyloxy)ethanone and 0.8 mg (0.001 mmol) of [R,R]-TsDPEN- RhCl-Cp*/Et$_3$N.HCl obtained in Preparation Example 2 were placed in a 10 ml round flask, and the flask was sealed. After introducing argon gas therein for 10 mins, 2.5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 97%).

$[\alpha]_D^{25}$=+44.9 (c=2.24, CHCl$_3$),
92.5% e.e.,
$^1$H NMR (300 MHz, CDCl$_3$) δ 7.75 (d, 2H, J=8.1), 7.35-7.23 (m, 6H), 4.99-4.94 (m, 1H), 4.15-3.99 (m, 2H), 2.45 (s, 3H).

Example 48

Preparation of (S)-(+)-1-(naphthalen-2-yl)-2-(p-tolylsulfonyloxy)ethanol 340 mg (1 mmol) of 1-(naphthalen-2-yl)-2-(p-tolylsulfonyloxy)ethanone and 0.8 mg (0.001 mmol) of [R,R]-TsDPEN-RhCl-Cp*/Et$_3$N.HCl obtained in Preparation Example 2 were placed in a 10 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 3 hrs and subjected to a column chromatography to obtain the title compound (yield: 98%).

$[\alpha]_D^{25}$=+49.2 (c=2.58, CHCl$_3$),
92.5% e.e.,
$^1$H NMR (300 MHz, CDCl$_3$) δ 7.83-7.72 (m, 6H), 7.51-7.47 (m, 2H), 7.38 (d, 1H, J=8.7), 7.27-7.25 (m, 2H), 5.15 (dd, 1H, J=3.3, 8.1), 4.27-4.11 (m, 2H), 2.45 (s, 3H).

Example 49

Preparation of (S)-(+)-1-(2-methoxy-5-methylphenyl)-2-(p-tolylsulfonyloxy)ethanol 334 mg (1 mmol) of 1-(2-methoxy-5-methylphenyl)-2-(p-tolylsulfonyloxy)ethanone and 1.5 mg (0.002 mmol) of [R,R]-TsDPEN-RhCl-Cp*/Et$_3$N.HCl obtained in Preparation Example 2 were placed in a 10 ml round flask, and the flask was sealed. After introducing argon gas therein for 10 mins, 4 ml of ethylacetate was added thereto to completely dissolve the starting materials, and 0.4 ml of a mixture of formic acid and triethylamine (5:2, molar ratio) were added thereto. When the color of the reaction mixture changed from light yellow to dark red after 2 to 3 mins, the reaction mixture was stirred at room temperature for 9 hrs and subjected to a column chromatography to obtain the title compound (yield: 76%).

$[\alpha]_D^{25}$=+32.8 (c=0.65, CHCl$_3$),
89.7% e.e. (this value was determined after converting the product to the acetate form),
$^1$H NMR (300 MHz, CDCl$_3$) δ 7.76 (2H, d, J=8.3 Hz), 7.32 (2H, d, J=8.0 Hz), 7.15 (1H, d, J=1.9 Hz), 7.05 (1H, dd, J=8.7 and 1.7 Hz), 6.71 (1H, d, J=8.3 Hz), 5.15-5.10 (1H, m), 4.25 (1H, dd, J=10.1 and 3.4 Hz), 4.05 (1H, dd, J=10.1 and 8.1 Hz), 3.73 (3H, s), 2.82 (1H, d, J=5.3 Hz), 2.44 (3H, s), 2.26 (3H, s).

Example 50

Preparation of (S)-2-(methanesulfonyloxy)-1-phenylethanol 0.215 g (1 mmol) of 2-(methanesulfonyloxy)-1-phenylethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 95%).

$[\alpha]_D^{29}$=+49.9 (c 1.05, CHCl$_3$),
97.3% e.e.,
$^1$H NMR (300 MHz, CDCl$_3$) δ 7.39-7.30 (5H, m), 5.03-4.98 (1H, m), 4.31 (1H, dd, J=10.8 and 3.7 Hz), 4.25 (1H, dd, J=10.8 and 7.8 Hz), 3.15 (1H, d, J=3.4 Hz), 2.99 (3H, s).

Example 51

Preparation of (S)-1-(3-chlorophenyl)-2-(methanesulfonyloxy)ethanol 0.246 g (1 mmol) of 1-(3-chlorophenyl)-2-(methanesulfonyloxy)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 45 mins and subjected to a column chromatography to obtain the title compound (yield: 97%).

$[\alpha]_D^{28}$=+40.0 (c 1.2, CHCl$_3$),
96.4% e.e.,
$^1$H NMR (300 MHz, CDCl$_3$) δ 7.41 (1H, s), 7.32-7.24 (3H, m), 5.04-4.99 (1H, m), 4.32 (1H, dd, J=10.9 and 3.4 Hz), 4.24 (1H, dd, J=10.8 and 8.0 Hz), 3.24 (1H, d, J=3.1 Hz), 3.04 (3H, s).

Example 52

Preparation of (S)-1-(4-methoxyphenyl)-2-(methanesulfonyloxy)ethanol 0.24 g (1 mmol) of 1-(4-methoxyphenyl)-2-(methanesulfonyloxy)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 5 ml of ethylacetate was added thereto to completely dissolve the starting materials, and 0.4 ml of a mixture of formic acid and triethylamine (5:2, molar ratio) was added thereto. The resulting mixture was stirred at room temperature for 4 hrs and subjected to a column chromatography to obtain the title compound (yield: 91%).

$[\alpha]_D^{25}$=+51.4 (c 1.10, CHCl$_3$),
97.2% e.e.,
$^1$H NMR (300 MHz, CDCl$_3$) δ 7.31 (2H, d, J=8.7 Hz), 6.91 (2H, d, J=8.4 Hz), 4.99 (1H, dd, J=7.5 and 4.5 Hz), 4.30 (1H, dd, J=11.1 and 4.5 Hz), 4.26-4.23 (1H, m), 3.81 (3H, s), 3.04 (3H, s).

Example 53

Preparation of (S)-2-(methanesulfonyloxy)-1-(naphthalene-2-yl)ethanol 0.266 g (1 mmol) of 2-(methanesulfonyloxy)-1-(naphthalene-2-yl)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 95%).

$[\alpha]_D^{28}$=+51.5 (c 0.55, CHCl$_3$), 99.2% e.e., $^1$H NMR (300 MHz, CDCl$_3$) δ 7.88-7.83 (4H, m), 7.52-7.46 (3H, m), 5.24-5.19 (1H, m), 4.44 (1H, dd, J=11.0 and 3.7 Hz), 4.37 (1H, dd, J=10.9 and 8.0 Hz), 3.04 (3H, s), 2.87 (1H, d, J=3.4 Hz).

Example 54

Preparation of (S)-1-(4-acetoxyphenyl)-2-(methanesulfonyloxy)ethanol 0.271 g (1 mmol) of 1-(4-acetoxyphenyl)-2-(methanesulfonyloxy)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 30 mins and subjected to a column chromatography to obtain the title compound (yield: 95%).

$[\alpha]_D^{26}$=+41.5 (c 1.02, CHCl$_3$), 97.4% e.e., $^1$H NMR (300 MHz, CDCl$_3$) δ 7.41 (2H, d, J=8.6 Hz), 7.10 (2H, d, J=8.47 Hz), 5.03-5.00 (1H, m), 4.31 (1H, dd, J=10.8 and 3.5 Hz), 4.24 (1H, dd, J=10.3 and 8.0 Hz), 3.02 (3H, s), 2.93 (1H, d, J=3.1 Hz), 2.30 (3H, s).

Example 55

Preparation of (S)-2-(methanesulfonyloxy)-1-(4-trifluoromethylphenyl)ethanol 0.280 g (1 mmol) of 2-(methanesulfonyloxy)-1-(4-trifluoromethylphenyl)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 20 mins and subjected to a column chromatography to obtain the title compound (yield: 98%).

$[\alpha]_D^{25}$=+37.7 (c 1.15, CHCl$_3$), 95.8% e.e., $^1$H NMR (300 MHz, CDCl$_3$) δ 7.66 (2H, d, J=8.1 Hz), 7.54 (2H, d, J=8.1 Hz), 5.14-5.11 (1H, m), 4.36 (1H, dd, J=10.8 and 3.3 Hz), 4.27 (1H, dd, J=11.1 and 8.1 Hz), 3.06 (3H, s), 2.88 (1H, d, J=3.6 Hz).

Example 56

Preparation of (S)-1-(4-fluorophenyl)-2-(methanesulfonyloxy)ethanol 0.235 g (1 mmol) of 1-(4-fluorophenyl)-2-(methanesulfonyloxy)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 40 mins and subjected to a column chromatography to obtain the title compound (yield: 95%).

$[\alpha]_D^{28}$=+47.5 (c 1.15, CHCl$_3$), 96.2% e.e., $^1$H NMR (300 MHz, CDCl$_3$) δ 7.41-7.34 (2H, m), 8.07 (2H, t, J=8.7 Hz), 5.06-5.01 (1H, m), 4.31 (1H, dd, J=10.9 and 3.7 Hz), 4.24 (1H, dd, J=10.9 and 8.0 Hz), 3.04 (3H, s), 2.96 (1H, d, J=3.4 Hz).

Example 57

Preparation of (S)-1-(3,4-di-chlorophenyl)-2-(methanesulfonyloxy)ethanol 0.285 g (1 mmol) of 1-(3,4-di-chlorophenyl)-2-(methanesulfonyloxy)ethanone and 0.8 mg (0.001 mmol) of [R,R]-TsDPEN-RhCl-Cp*/Et$_3$N.HCl obtained in Preparation Example 2 were placed in a 25 ml round flask, and the flask was sealed. After introducing argon gas therein for 10 mins, 2 ml of ethylacetate was added thereto to completely dissolve the starting materials, and 0.2 ml of a mixture of formic acid and triethyamine (5:2, molar ratio) was added thereto. The resulting mixture was stirred at room temperature for 1 hr and subjected to a column chromatography to obtain the title compound (yield: 97%).

$[\alpha]_D^{25}$=+37.3 (c 1.02, CHCl$_3$), 93.7% e.e., $^1$H NMR (300 MHz, CDCl$_3$) δ 7.52 (1H, d, J=1.7 Hz), 7.46 (1H, d, J=8.3 Hz), 7.26 (1H, dd, J=8.3 and 1.7 Hz), 5.03-5.00 (1H, m), 4.32 (1H, dd, J=10.9 and 3.3 Hz), 4.22 (1H, dd, J=10.9 and 8.2 Hz), 3.06 (3H, s), 2.95 (1H, s).

Example 58

Preparation of (S)-(+)-2-chloro-1-phenylethanol 155 mg (1 mmol) of 2-chloro-1-phenylethanone and 2 mg (0.002 mmol) of [R,R]-TsDPEN-RhCl-Cp* obtained in Preparation Example 3 were placed in a 10 ml round flask, and the flask was sealed. After introducing argon gas therein for 10 mins, 1 ml of ethylacetate was added thereto to completely dissolve the starting materials, and 0.2 ml of a mixture of formic acid and triethyamine (5:2, molar ratio) was added thereto. After 2 hrs, the reaction mixture was directly loaded on a silica gel (200 mesh) column using 15% EtOAc/hexane as an eluent to obtain 148 mg of the title compound as an liquid (yield: 95%).

$[\alpha]_D^{25}$=+41.6 (c=5.02, $C_6H_{12}$), 95.3% e.e., $^1$H NMR (300 MHz, CDCl$_3$) δ 7.39-7.29 (5H, m); 4.92 (1H, d, J=5.7 Hz); 3.72 (1H, dd, J=11.4 and 3.6 Hz); 3.68 (1H, dd, J=8.7 and 2.4 Hz); 2.64 (OH, d, J=2.7 Hz).

Example 59

Preparation of (R)-(−)-2-chloro-1-phenylethanol 154 mg (1 mmol) of 2-chloro-1-phenylethanone and 0.6 mg (0.001 mmol) of the compound obtained in Preparation Example 4 were placed in a 10 ml round flask, and the flask was sealed. After introducing argon gas therein for 10 mins, 2 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 1.5 hrs and subjected to a column chromatography to obtain the title compound (yield: 93%).

$[\alpha]_D^{25}$=−45.2 (c=2.63, CHCl$_3$), 97.0% e.e., $^1$H NMR (300 MHz, CDCl$_3$) δ 7.39-7.30 (m, 5H), 4.93-4.88 (m, 1H), 3.78-3.62 (m, 2H).

Example 60

Preparation of (R)-(−)-1-phenyl-2-(p-tolylsulfonyloxy)ethanol 290 mg (1 mmol) of 1-phenyl-2-(p-tolylsulfonyloxy)ethanone and 0.6 mg (0.001 mmol) of the compound obtained in Preparation Example 4 were placed in a 10 ml round flask, and the flask was sealed. After introducing argon gas therein for 10 mins, 2 ml of ethylacetate was added thereto to completely dissolve the starting materials, and 0.2 ml of a mixture of formic acid and triethylamine (5:2, molar ratio) were added thereto. When the color of the reaction mixture changed from light yellow to dark red after 2 to 3 mins, the reaction mixture was stirred at room temperature for 2 hrs and subjected to a column chromatography to obtain the title compound (yield: 96%).

$[\alpha]_D^{25}$=−51.6 (c=1.24, CHCl$_3$), 95.9% e.e., $^1$H NMR (300 MHz, CDCl$_3$) δ 7.77 (d, 2H, J=8.1), 7.42-7.28 (m, 7H), 5.00-4.96 (m, 1H), 4.18-4.01 (m, 2H), 2.45 (s, 3H).

While the invention has been described with respect to the above specific embodiments, it should be recognized that various modifications and changes may be made to the invention by those skilled in the art which also fall within the scope of the invention as defined by the appended claims.

What is claimed is:

1. A method for preparing an optically active 2-sulfonyloxy-1-phenylethanol derivative of formula (II), comprising i) reacting (pentamethylcyclopentadienyl)rhodium(III) chloride dimer ([Rh(C$_5$Me$_5$)Cl$_2$]$_2$) with optically active 1,2-diphenylethylene-N-(p-toluenesulfonyl)diamine in methylene chloride as a solvent and optionally in the presence of triethylamine, and removing the solvent from the reaction product to obtain a rhodium compound having pentamethylcyclopentadienyl group; and ii) subjecting an α-sulfonyloxy acetophenone compound to asymmetrical reduction in the presence of the rhodium compound having pentamethylcyclopentadienyl group as a catalyst and a hydrogen donor:

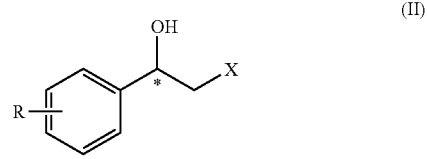

wherein,

X is tosyloxy or mesyloxy;

R is one or more substituents, each independently, selected from the group consisting of H, F, Cl, Br, OH, OMe, OBn, OAc, OTBS, OTs, NH$_2$, NHBn, NHBz, NHTBS, NHMs, N(Ac)$_2$, N(Ms)$_2$, NO$_2$, CF$_3$, Me, tert-Bu and CH$_2$OMe, substituted in the ortho-, metha- or para-position of the phenyl moiety, the substituents being optionally fused together to form a benzene, dioxane or dioxolane ring, wherein Me=methyl, Bn=benzyl, Bu=butyl, Bz=benzoyl, TBS=tert-butyldimethylsilyl, Ms=mesyl, Ac=acetyl, and Ts=tosyl.

2. The method of claim 1, wherein the rhodium compound having pentamethylcyclopentadienyl group is represented by formula (V) or (VI):

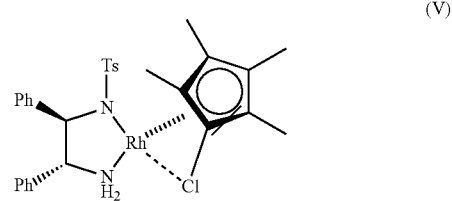

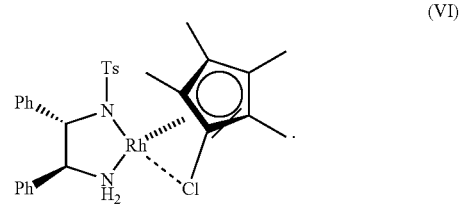

3. The method of claim 1, wherein the hydrogen donor is formic acid, a metal or ammonium salt thereof, or an azeotropic mixture of formic acid and an amine.

* * * * *